(12) United States Patent
Chung et al.

(10) Patent No.: US 9,795,649 B2
(45) Date of Patent: Oct. 24, 2017

(54) **SESQUITERPENOID-BASED COMPOUNDS, EXTRACTS OF *CYPERUS ROTUNDUS* COMPRISING THE SAME, AND USE THEREOF**

(71) Applicant: RESEARCH & BUSINESS FOUNDATION SUNGKYUNKWAN UNIVERSITY, Suwon-si (KR)

(72) Inventors: Kyu Hyuck Chung, Siheung-si (KR); Jong Hwan Kwak, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 242 days.

(21) Appl. No.: 14/517,136

(22) Filed: Oct. 17, 2014

(65) Prior Publication Data
US 2015/0110901 A1  Apr. 23, 2015

(30) Foreign Application Priority Data

Oct. 21, 2013 (KR) .................. 10-2013-0125593
Oct. 21, 2013 (KR) .................. 10-2013-0125594

(51) Int. Cl.
| | |
|---|---|
| *A61K 36/89* | (2006.01) |
| *A61K 36/8905* | (2006.01) |
| *A61K 31/336* | (2006.01) |
| *A61K 31/122* | (2006.01) |
| *A61K 31/045* | (2006.01) |
| *A61K 31/075* | (2006.01) |
| *A23L 33/105* | (2016.01) |

(52) U.S. Cl.
CPC ........ *A61K 36/8905* (2013.01); *A23L 33/105* (2016.08); *A61K 31/045* (2013.01); *A61K 31/075* (2013.01); *A61K 31/122* (2013.01); *A61K 31/336* (2013.01); *A61K 2236/00* (2013.01)

(58) Field of Classification Search
None
See application file for complete search history.

(56) References Cited

U.S. PATENT DOCUMENTS

2010/0260875 A1* 10/2010 Mitra .................. A61K 9/0095
424/773

FOREIGN PATENT DOCUMENTS

| KR | 20100024332 A | * | 9/2011 |
| KR | 10-2013-0102181 A | | 9/2013 |

OTHER PUBLICATIONS

Hikino, Hiroshi et al. "4α, 5α-Oxidoeudesm-11-En-3α-Ol, Sesouiterpenoid of Cyperus Rotundus." *Phytochemistry* 15.8 (1976): pp. 1265-1266.
Hikino, Hiroshi et al. "Synthesis of Cyperolone and 3-epi-Cyperolone," *Chemical & pharmaceutical bulletin* 15.9 (1967): pp. 1395-1404.
Haaksma, A. A., Jansen, B. J., & de Groot, A. (Feb. 1992). "Lewis Acid catalyzed Diels-Alder Reactions of S-(+)-Carvone[1] with Silyloxy Dienes. Total Synthesis of (+)-α-Cyperone,".*Tetrahedron*, vol. 48 No. 15, pp. 3121-3130.
Kiuchi; Fumiyuki et al. "Inhibition of Prostaglandin Biosynthesis by the Constituents of Medicinal Plants." *Chemical & pharmaceutical bulletin* 31.10 (1983): pp. 3391-3396.
Thebtaranonth, C., et al. "Antimalarial Sesquiterpenes from Tubers of Cyperus Rotunolus: Structure of 10, 12-Peroxycalamenene, a Sesquiterpene Endoperoxide," *Phytochemistry* 40.1 (1995): pp. 125-128.
Xu, Yan, et al. "Complete assignments of $^1$H and $^{13}$C NMR data for two new sesquiterpenes from *Cyperus rotundus* L." *Magnetic resonance in chemistry* 47.6 (Mar. 2009): pp. 527-531.
Su Jung Kim, "Sesquiterpenes isolated from the Rhizomes of Cyperus rotundus". Department of Oriental Pharmaceutical Sciences, Graduate School, Kyung Hee University (Feb. 2013) 58 pages.
Kim, Su Jung, et al. "Sesquiterpenes from the Rhizomes of Cyperus rotundus and Their Potential to Inhibit LPS-induced Nitric Oxide Production." *Bull. Korean Chem. Soc.* vol. 34, No. 7 (2013): pp. 2207-2210.
Korean Office Action dated Jul. 29, 2014 in counterpart Korean Patent Application No. 10-2013-0125593 (8 pages, in Korean).
Korean Office Action dated Sep. 17, 2014 in counterpart Korean Patent Application No. 10-2013-0125594 (5 pages, in Korean).
Korea Research Council of Pharmacognosy, "Modern Pharmacognosy," Hakchangsa, 1994 (8 pages).
Korean Notice of Allowance dated Jan. 9, 2015, in counterpart Korean Application No. 10-2013-0125593.
Korean Notice of Rejection dated Feb. 13, 2015, in counterpart Korean Application No. 10-2013-0125594.

* cited by examiner

*Primary Examiner* — Chris R Tate
*Assistant Examiner* — Randall Winston
(74) *Attorney, Agent, or Firm* — NSIP Law

(57) ABSTRACT

The present invention relates to a novel use of sesquiterpenoid compounds, the pharmaceutically acceptable salts thereof, or the extracts of *Cyperus rotundus* comprising same or the fractions thereof in the prevention or treatment of menopausal diseases.

The sesquiterpenoid compound according to the present invention, the extracts of *Cyperus rotundus* comprising the same or fractions thereof exhibit excellent estrogenic activity or anti-allergic activity, and therefore they can be used for the prevention or treatment of menopausal diseases caused by a decline in estrogen level or by allergic diseases.

2 Claims, 13 Drawing Sheets

[FIG. 1]
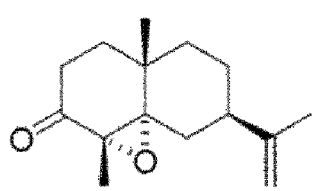
[1]
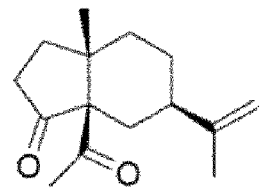
[2]
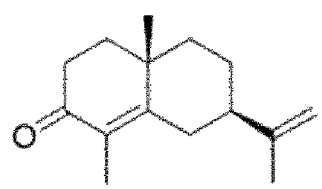
[3]
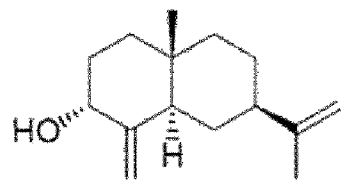
[4]
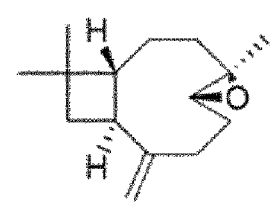
[5]
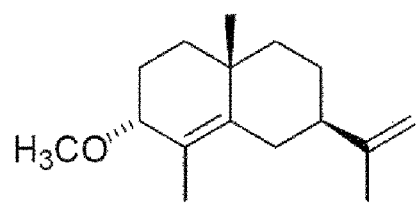
[6]
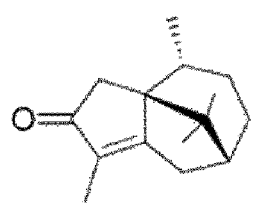
[7]

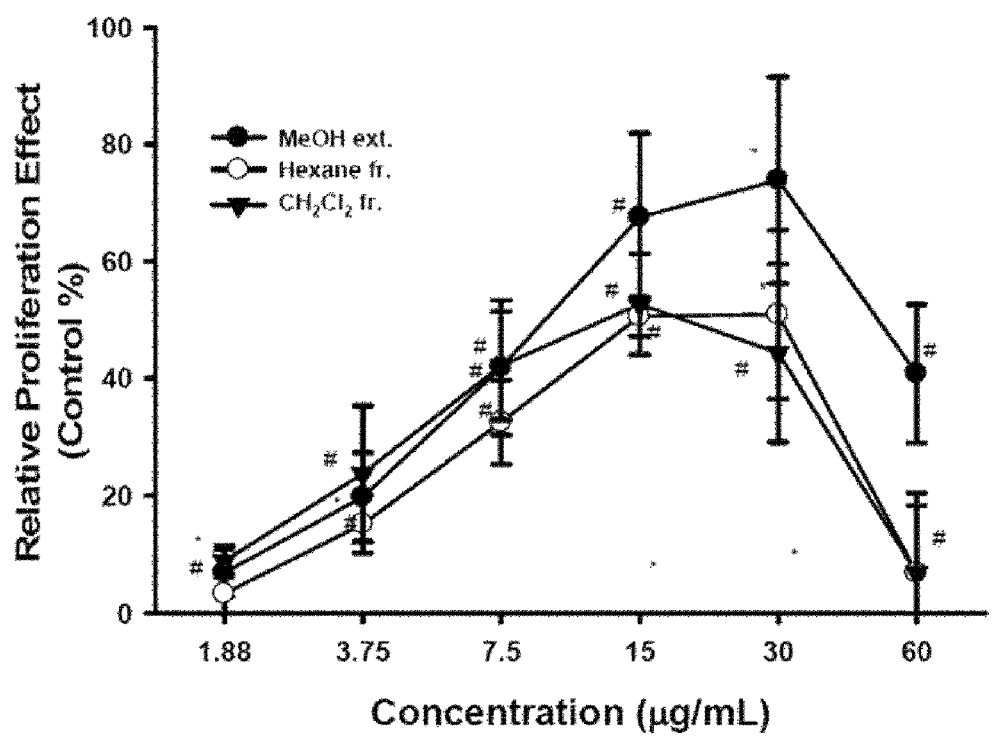
[FIG. 2]

[FIG. 3A]
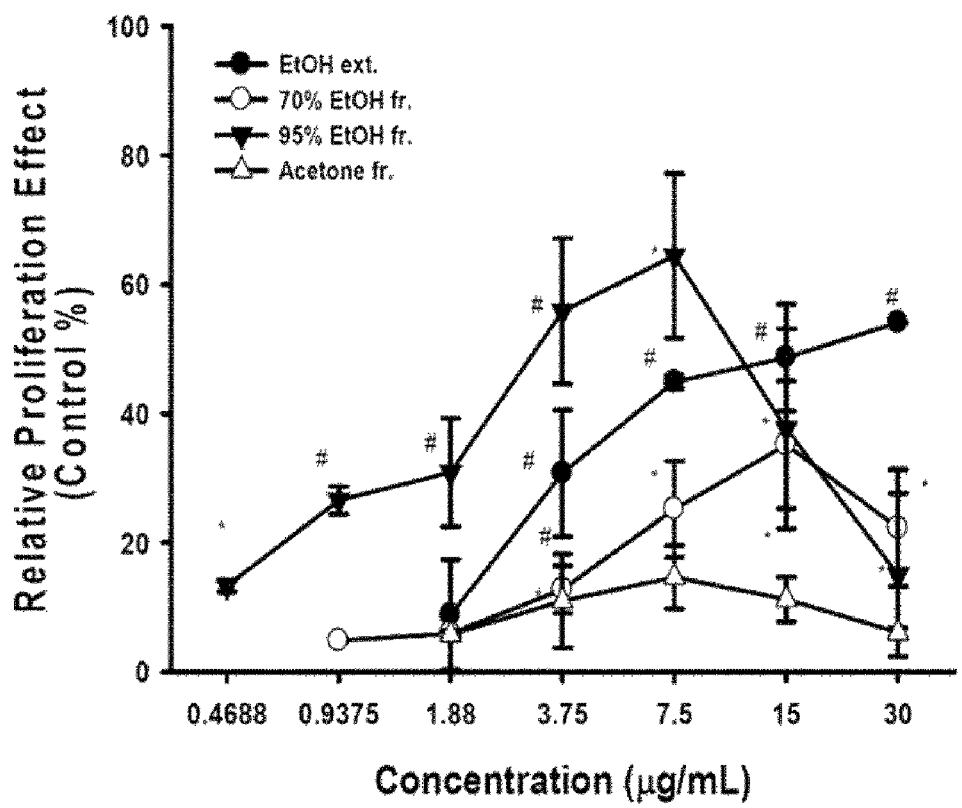

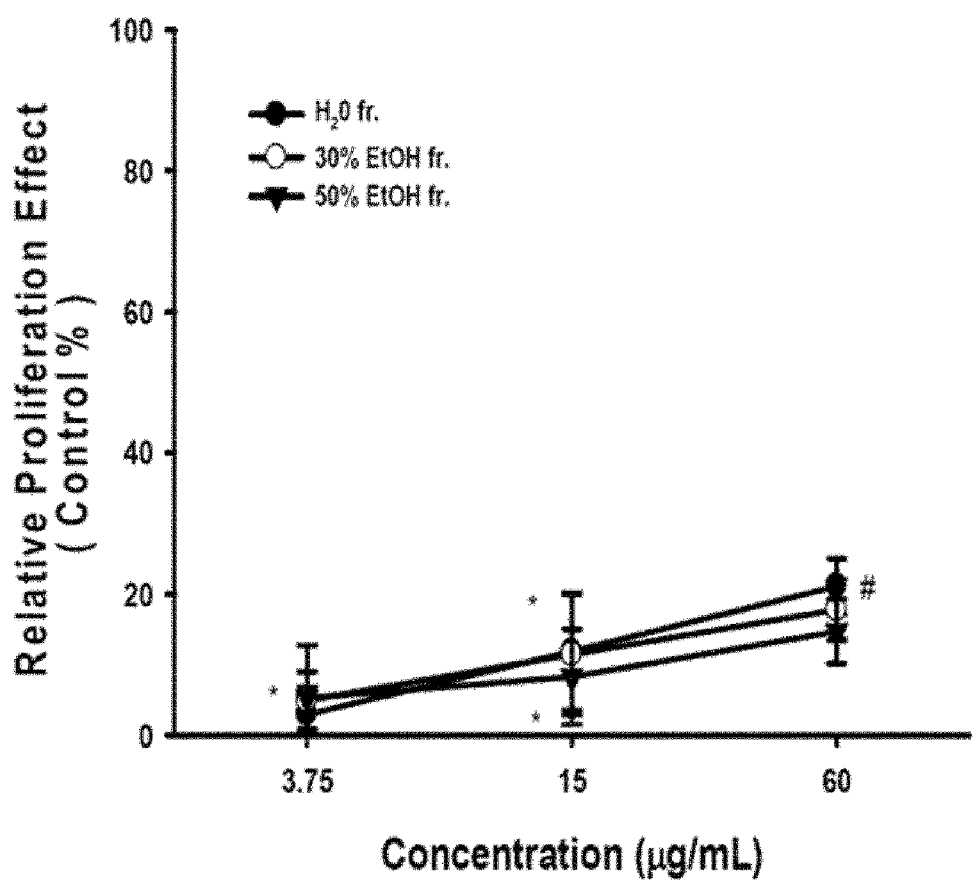

[FIG. 4A]
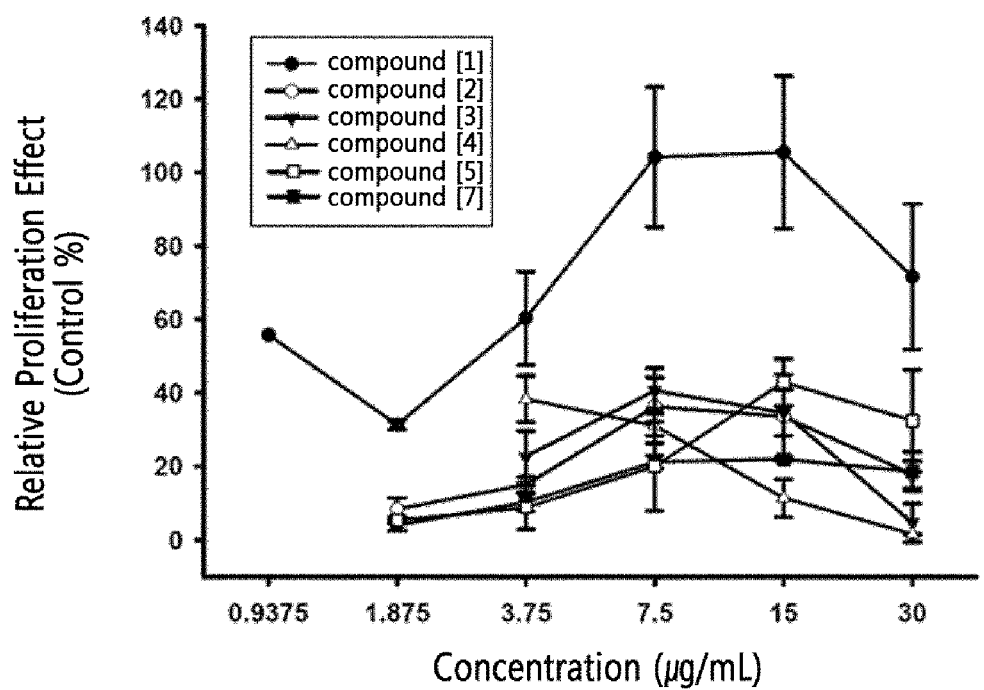

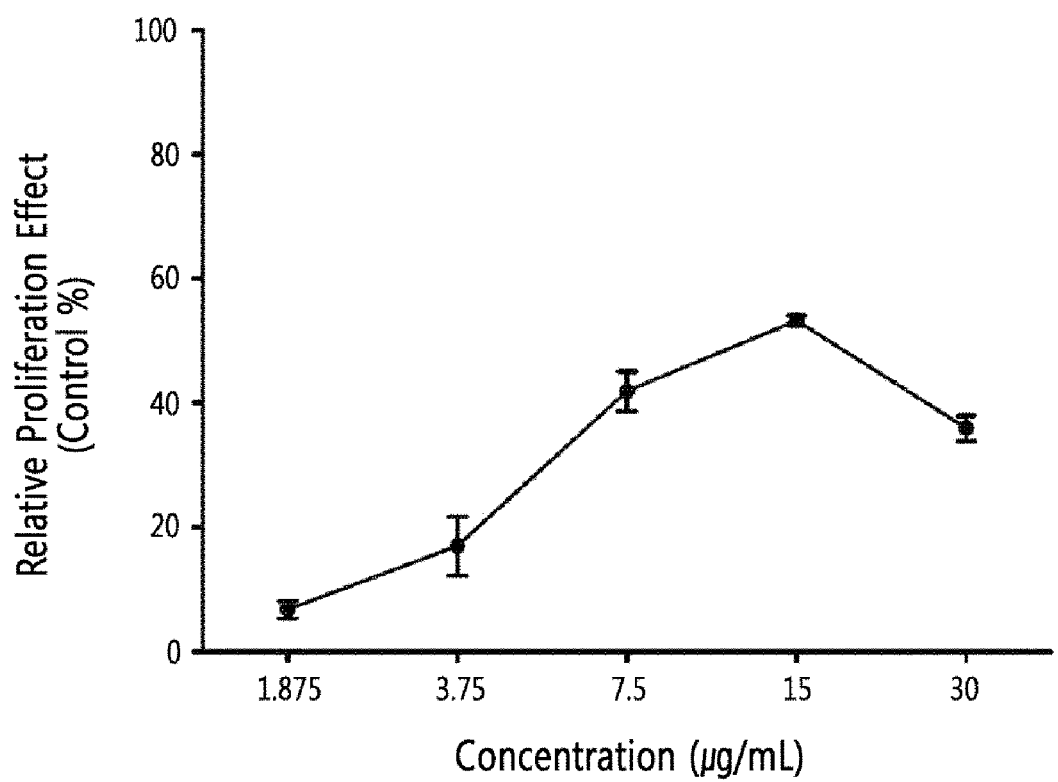
[FIG. 4B]

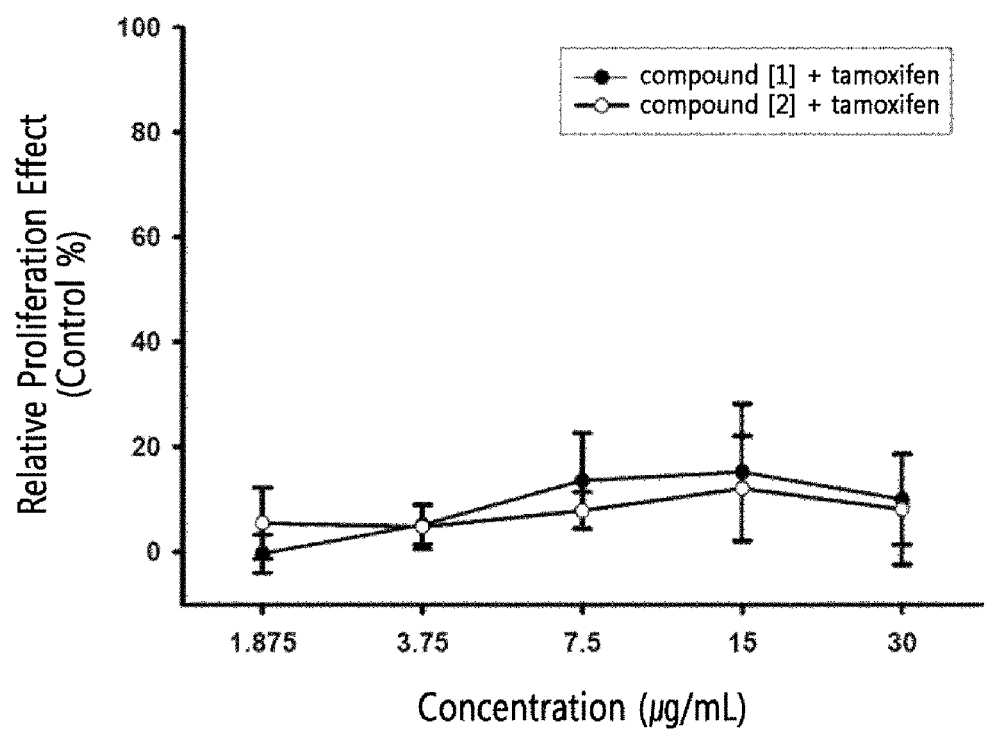
[FIG. 5A]

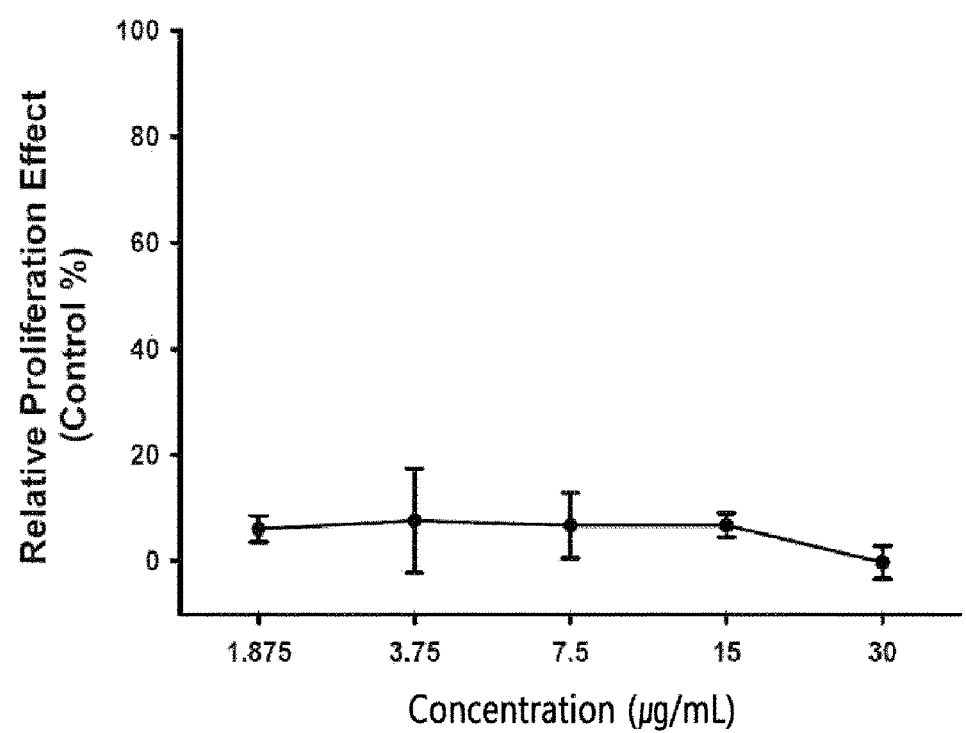
[FIG. 5B]

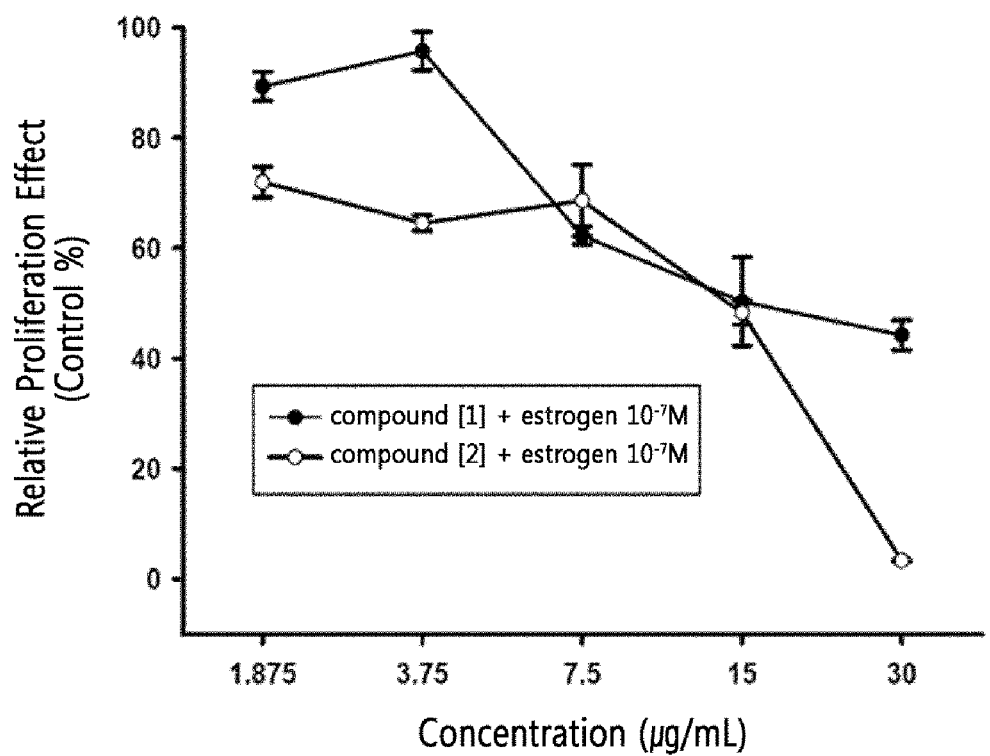
[FIG. 6A]

[FIG. 6B]
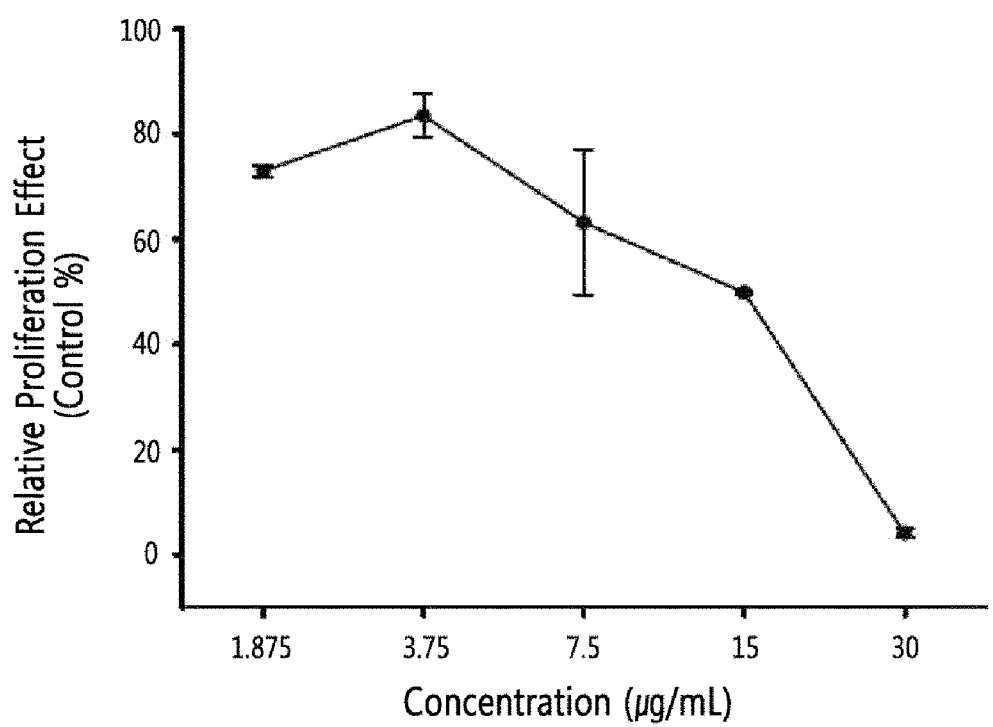

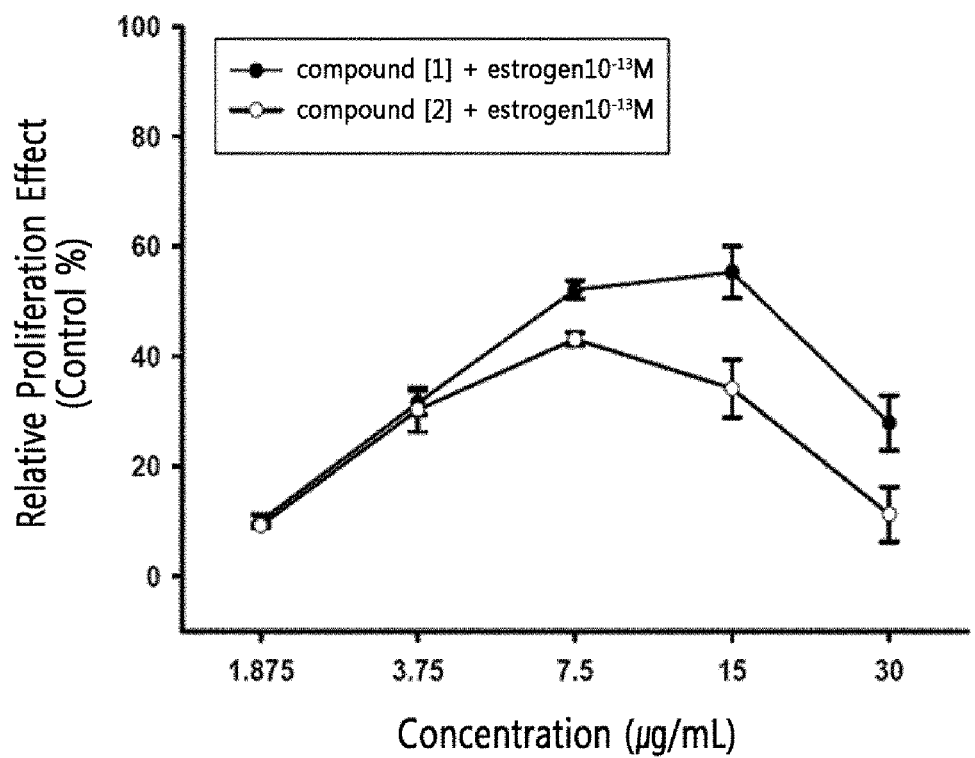
[FIG. 7A]

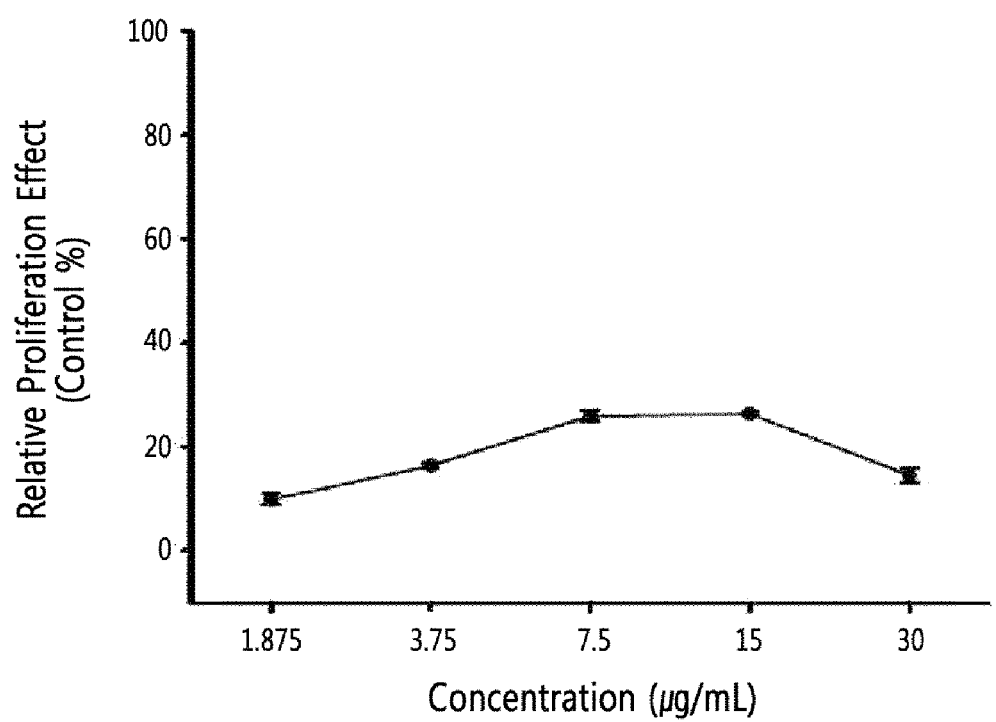
[FIG. 7B]

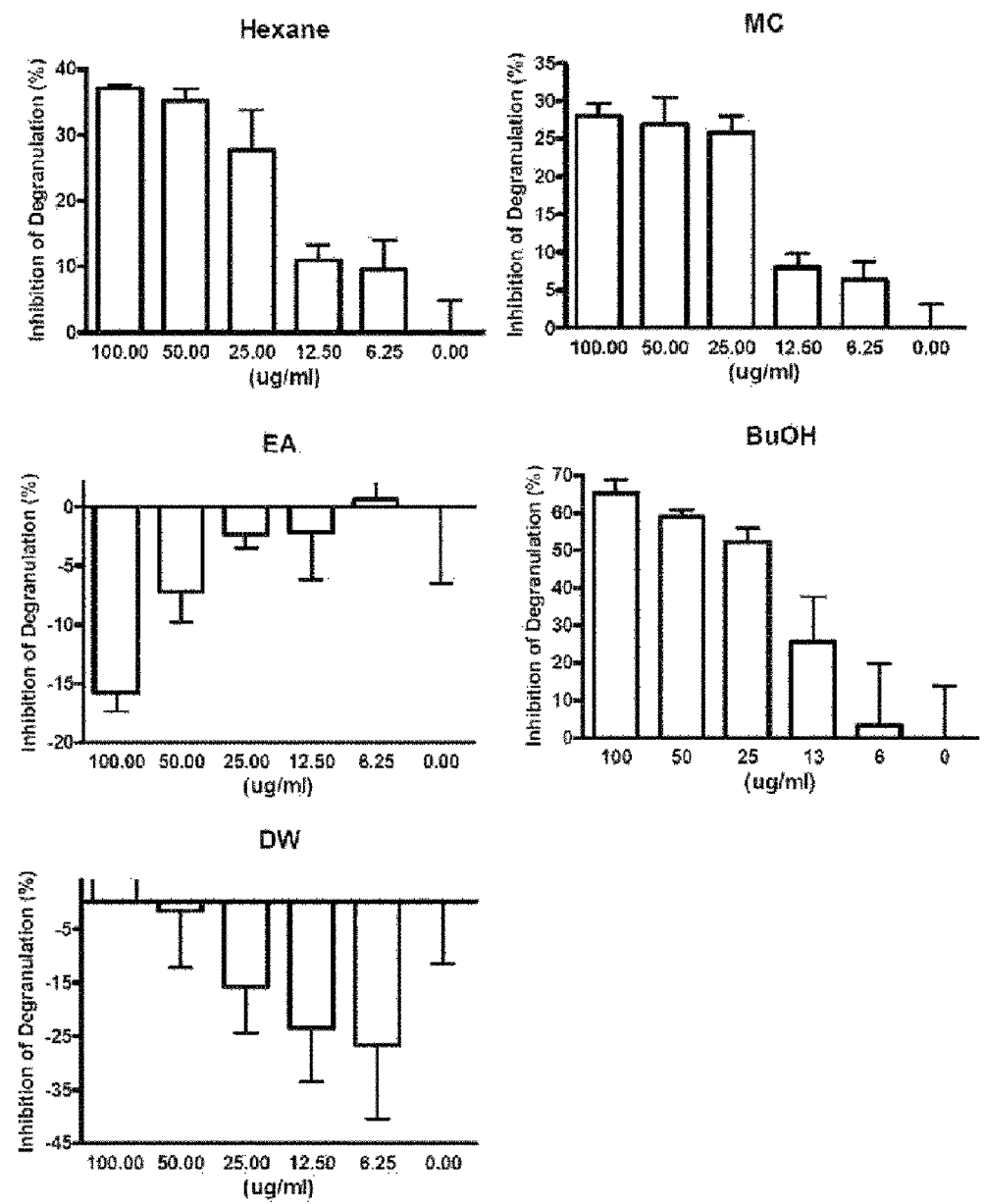
[FIG. 9]

SESQUITERPENOID-BASED COMPOUNDS, EXTRACTS OF *CYPERUS ROTUNDUS* COMPRISING THE SAME, AND USE THEREOF

CROSS-REFERENCE TO RELATED APPLICATIONS

This application claims the benefit under 35 U.S.C. 119(a) of Korean Patent Application No. 10-2013-0125593 filed on Oct. 21, 2013 and Korean Patent Application No. 10-2013-0125594 filed on Oct. 21, 2013 in the Korean Intellectual Property Office, the entire disclosure of which is incorporated herein by reference for all purposes.

BACKGROUND

1. Field

The present invention relates to use of a sesquiterpenoid-based compounds having an estrogenic activity or a pharmaceutically acceptable salt thereof, or extracts of *Cyperus rotundus* comprising the same or a fraction thereof in the prevention and treatment of menopausal disease.

2. Description of Related Art

As women get older, ovarian functions deteriorate, ovulation and production of female sex hormones eventually stop. Menopause is usually diagnosed by the absence of menstruation for 1 year. Typically, these changes occur in the mid-to-late 40s, and gradually progress. A term for about 1 year after onset of menopause at which menstruation stops completely is called menopausal transition, more often, climacterium. It lasts for about 4~7 years on average. Menopause, itself, occurs as a result of ovarian aging, and menopause, rather than being an illness, is a natural change in the body. A Menopausal disorder is caused by a decline in the level of estrogen, a female hormone having various functions of helping blood circulation, body weight regulation, bone maintenance as well as female sexual characteristics around the age of 50 in the climacteric period. It is known that the same symptoms also occur in estrogen-deficient patients due to other causes such as oophorectomy or decline in ovarian functions, besides climacterium.

A menopausal disorder causes neuropsychiatric symptoms such as poor concentration, insomnia, headache, tinnitus, nervousness, etc., as well as changes in the body such as abdominal obesity, atrophy of uterus, cognitive impairment, blood flow disorder, skin aging, etc., and therefore, it is a main cause of reducing quality of life. With a growing population of post-menopausal women, their cardiovascular diseases and osteoporosis have been prevented and treated by a hormone replacement therapy using female hormones, estrogen and progestin. However, long-term use of the hormone replacement therapy may cause adverse effects including risk of breast cancer. Therefore, the hormone replacement therapy used for severe menopausal diseases should be implemented considering the possibility of various complications. For this reason, phytoestrogens have been attempted in some cases, but their efficacies are weaker than that of estrogen, and may induce breast cancer upon excessive exposure thereto. Accordingly, there has been demand to develop phytoestrogens capable of exhibiting estrogenic effects, thereby preventing or treating menopausal disorders, while showing no excessive effects, thereby reducing the risk of breast cancer.

Meanwhile, allergy is a biochemical phenomenon showing a specific and altered reaction against a foreign substance. During allergic reaction, various cytokines are released to cause allergy-specific symptoms. In this regard, the allergy-producing substances are called allergens. The etiology of allergy is a pathological process in the body resulting from antigen-antibody reaction, and allergy is generally classified into 1 of 4 types according to time taken for the reaction and complement mediation.

During allergic reaction, IgE is produced from B-cells by a helper T-cell which has already become activated by a foreign antigen presented by a macrophage, and IgE thus produced binds to a high-affinity IgG receptor (FcRIa) on a mast cell membrane. Cross-linking between antigens such as ticks or pollens and a plurality of the bound IgE antibodies triggers receptor aggregation, and mast cells are activated by the cross-linking and aggregation. An increase in cytosolic calcium ion ($Ca^{2+}$) levels in the activated mast cells causes degranulation. In turn, degranulation causes the release of chemical transmitters such as histamine from mast cells and the release of prostaglandin, leukotriene, etc. which are newly synthesized, at the same time. The chemical transmitters released by degranulation include NCF (neutrophil chemotactic factor), ECF (eosinophil chemotactic factor), and PAF (platelet activating factor) which act as chemotactic factors of inflammatory cells such as eosinophils, neutrophils, etc. in addition to histamine having functions of arteriolar dilation, increased capillary permeability, contraction of bronchial smooth muscle, or secretion enhancement, serotonin, and leukotriene. Allergic reaction is mediated by theses chemical transmitters.

A therapeutic or prophylactic agent for allergy is largely divided into a steroidal anti-inflammatory agent or a non-steroidal anti-inflammatory agent and antihistamines or anti-leukotrienes. The former has a strong immunosuppressive action showing a temporary sedative effect within a short period of time, but its long-term use generates many problems from mild side-effects such as nausea, to severe side-effects such as growth inhibition or osteoporosis. The latter can show a temporary sedative effect, but its use is restricted because of side-effects of sleepiness, dizziness, etc. Therefore, studies have been actively conducted to develop compounds enabling safe applications with high efficacies and effects.

The present inventors have made many efforts to investigate a substance capable of exhibiting an estrogenic activity and/or an anti-allergic activity with fewer side-effects. As a result, they investigated a sesquiterpenoid compound showing an estrogenic activity or an anti-allergic activity from an extract of *Cyperus rotundus*. They found that this sesquiterpenoid compound is an estrogen agent having fewer side-effects, and has an advantage of being used for the prevention or treatment of menopausal disorders. They also investigated an extract of *Cyperus rotundus* and a fraction thereof which includes the above compound to show excellent estrogenic activity and/or the anti-allergic activity, and they found that the compound or the extract of *Cyperus rotundus* comprising the compound, and the fraction thereof can be used for the prevention and treatment of menopausal disorders or allergic diseases, thereby completing the present invention.

SUMMARY

An objective of the present invention is to provide a method for preventing or treating a menopausal disorder in a subject in need thereof, said method comprising administering (a) a compound represented by any one of the following Chemical Formulae 1 to 6 or a pharmaceutically acceptable salt thereof, or (b) an extract of *Cyperus rotundus* comprising (a) or a fraction thereof to the subject.

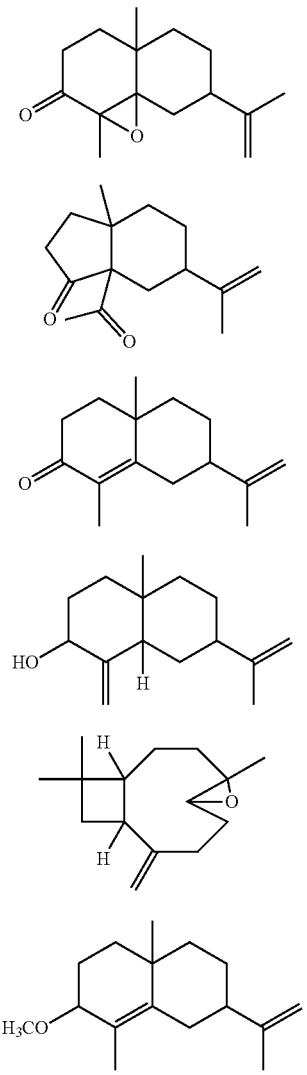

[Chemical Formula 1]

[Chemical Formula 2]

[Chemical Formula 3]

[Chemical Formula 4]

[Chemical Formula 5]

[Chemical Formula 6]

In one embodiment, the method of the present invention is characterized in that the extract is obtained by extraction of *Cyperus rotundus* with C1-C4 alcohol.

In another embodiment, the method of the present invention is characterized in that the fraction is an organic solvent fraction of a C1-C4 alcohol extract of *Cyperus rotundus*.

In still another embodiment, the method of the present invention is characterized in that the organic solvent is selected from the group consisting of isopropanol, butanol, ethylene, acetone, hexane, ether, chloroform, ethyl acetate, butyl acetate, dichloromethane, N,N-dimethyl formamide (DMF), dimethyl sulfoxide (DMSO), 1,3-buthylene glycol, propylene glycol, and solvent mixtures thereof.

In still another embodiment, the method of the present invention is characterized in that the menopausal disorder is accompanied by one or more symptoms selected from the group consisting of hot flashes, sudation, skin dryness, vaginal dryness, vaginal atrophy, atrophy of the lower urinary tract, dyspareunia, vaginitis, cystitis, dysuria, urinary urgency, attention deficit disorder, short-term memory impairment, anxiety, nervousness, memory loss, hypoactive sexual desire disorder, myalgia, arthralgia, and osteoporosis.

In still another embodiment, the method of the present invention is characterized in that the compound represented by any one of Chemical Formulae 1 to 6 has an estrogenic activity.

Another objective of the present invention is to provide a compound represented by Chemical Formula 6 or a pharmaceutically acceptable salt thereof.

Still another objective of the present invention is to provide a pharmaceutical composition for the prevention or treatment of a menopausal disorder, comprising (a) the compound represented by Chemical Formula 6 or a pharmaceutically acceptable salt thereof, or (b) an extract of *Cyperus rotundus* comprising (a) or a fraction thereof as an active ingredient.

In one embodiment, the pharmaceutical composition of the present invention is characterized in that the extract is obtained by extraction of *Cyperus rotundus* with C1-C4 alcohol.

In another embodiment, the pharmaceutical composition of the present invention is characterized in that the fraction is an organic solvent fraction of a C1-C4 alcohol extract of *Cyperus rotundus*.

In still another embodiment, the pharmaceutical composition of the present invention is characterized in that the organic solvent is selected from the group consisting of isopropanol, butanol, ethylene, acetone, hexane, ether, chloroform, ethyl acetate, butyl acetate, dichloromethane, N,N-dimethyl formamide (DMF), dimethyl sulfoxide (DMSO), 1,3-buthylene glycol, propylene glycol, and solvent mixtures thereof.

In still another embodiment, the pharmaceutical composition of the present invention is characterized in that the menopausal disorder is accompanied by one or more symptoms selected from the group consisting of hot flashes, sudation, skin dryness, vaginal dryness, vaginal atrophy, atrophy of the lower urinary tract, dyspareunia, vaginitis, cystitis, dysuria, urinary urgency, attention deficit disorder, short-term memory impairment, anxiety, nervousness, memory loss, hypoactive sexual desire disorder, myalgia, arthralgia, and osteoporosis.

Still another objective of the present invention is to provide a food composition for the prevention or improvement of a menopausal disorder, comprising (a) the compound represented by Chemical Formula 6 or a pharmaceutically acceptable salt thereof, or (b) an extract of *Cyperus rotundus* comprising (a) or a fraction thereof as an active ingredient.

Still another objective of the present invention is to provide a quasi-drug composition for the prevention or improvement of a menopausal disorder, comprising (a) the compound represented by Chemical Formula 6 or a pharmaceutically acceptable salt thereof, or (b) an extract of *Cyperus rotundus* comprising (a) or a fraction thereof as an active ingredient.

Still another objective of the present invention is to provide a pharmaceutical composition for the prevention or treatment of an allergic disease, comprising (a) the compound represented by Chemical Formula 6 or a pharmaceutically acceptable salt thereof, or (b) an extract of *Cyperus rotundus* comprising (a) or a fraction thereof as an active ingredient.

In one embodiment, the pharmaceutical composition of the present invention is characterized in that the allergic disease is atopy, asthma, hypersensitivity, allergic rhinitis, allergic conjunctivitis, allergic dermatitis, contact dermatitis, hives, insect allergies, food allergies, or drug allergies.

Still another objective of the present invention is to provide a method for preventing or treating an allergic disease in a subject in need thereof, comprising administering (a) a compound represented by Chemical Formula 6 or a pharmaceutically acceptable salt thereof, or (b) an extract of *Cyperus rotundus* comprising (a) or the fraction thereof to the subject.

Still another objective of the present invention is to provide a food composition for the prevention or improvement of an allergic disease, comprising (a) the compound represented by Chemical Formula 6 or a pharmaceutically acceptable salt thereof, or (b) an extract of *Cyperus rotundus* comprising (a) or the fraction thereof as an active ingredient.

Still another objective of the present invention is to provide a quasi-drug composition for the prevention or improvement of an allergic disease, comprising (a) the compound represented by Chemical Formula 6 or a pharmaceutically acceptable salt thereof, or (b) an extract of *Cyperus rotundus* comprising (a) or the fraction thereof as an active ingredient.

Still another object of the present invention is to provide a method for preventing or treating a menopausal disorder or an allergic disease in a subject in need thereof, said method comprising administering (a) a dichloromethane or butanol fraction of a C1-C4 alcohol extract of *Cyperus rotundus*, or (b) an ethanol fraction thereof to the subject, wherein said (b) ethanol fraction is obtained by subjecting the C1-C4 alcohol extract of *Cyperus rotundus* to hydrophobic chromatography and eluting it with a 70 to 90% ethanol solution.

BRIEF DESCRIPTION OF THE DRAWINGS

FIG. 1 shows 7 types of sesquiterpenoid compounds separated from an extract of *Cyperus rotundus*;

FIG. 2 shows estrogenic activities of methanol extract of *Cyperus rotundus* and solvent fractions thereof;

FIG. 3A shows estrogenic activities of an ethanol extract of *Cyperus rotundus* and fractions thereof (70% ethanol fraction, 95% ethanol fraction, and acetone fraction);

FIG. 3B shows estrogenic activities of an ethanol extract of *Cyperus rotundus* and fractions thereof (water fraction, 30% ethanol fraction, and 50% ethanol fraction);

FIG. 4A shows the results of examining estrogenic activities of Compounds [1] to [5] and [7] separated from an extract of *Cyperus rotundus*;

FIG. 4B shows the result of examining estrogenic activity of Compound [6];

FIG. 5A shows the results of examining estrogenic activities of Compounds [1] and [2] by co-treatment of Tamoxifen;

FIG. 5B shows the result of examining estrogenic activity of Compound [6] by co-treatment of Tamoxifen;

FIG. 6A shows changes in estrogenic activities of Compounds [1] and [2] by co-treatment of high concentration of estrogen;

FIG. 6B shows a change in estrogenic activity of Compound [6] by co-treatment of high concentration of estrogen ($10^{-7}$M);

FIG. 7A shows changes in estrogenic activities of Compounds [1] and [2] by co-treatment of low concentration of estrogen;

FIG. 7B shows a change in estrogenic activity of Compound [6] by co-treatment of low concentration of estrogen ($10^{-13}$ M); and FIG. 8 shows anti-allergic activities of solvent fractions of methanol extract of *Cyperus rotundus* (hexane, dichloromethane (MC), ethyl acetate (EA), butanol (BuOH), and distilled water (DW)).

DETAILED DESCRIPTION

One aspect of the present invention provides a method for preventing or treating a menopausal disorder in a subject in need thereof, said method comprising administering (a) a compound represented by any one of the following Chemical Formulae 1 to 6 or a pharmaceutically acceptable salt thereof, or (b) an extract of *Cyperus rotundus* comprising (a) or a fraction thereof to the subject.

[Chemical Formula 1]

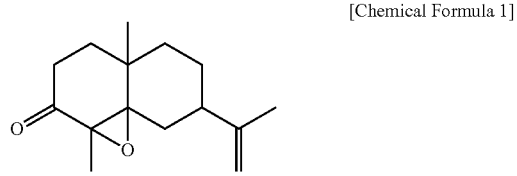

[Chemical Formula 2]

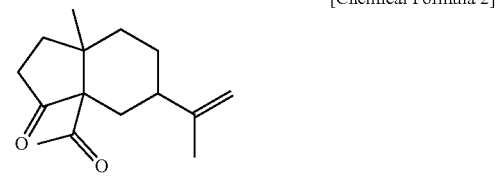

[Chemical Formula 3]

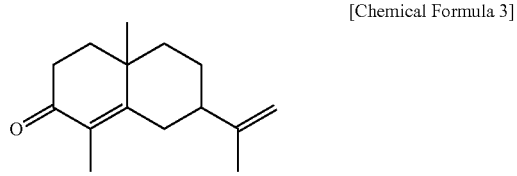

[Chemical Formula 4]

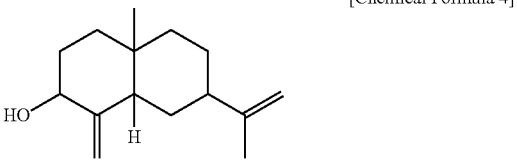

[Chemical Formula 5]

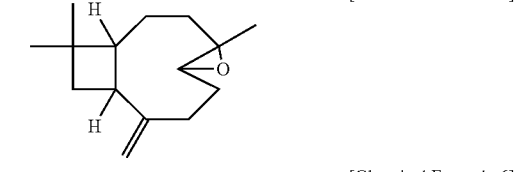

[Chemical Formula 6]

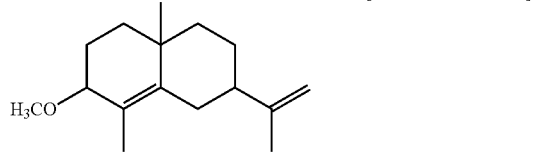

In the present invention, 6 types of compounds showing phytoestrogenic efficacy were investigated from fractions of the extract of *Cyperus rotundus* having a high estrogenic activity. The compounds represented by Chemical Formulae 1 to 5 are designated as 4α,5α-oxidoeudesm-11-en-3-one (Compound [1]), cyper-11-ene-3,4-dione (Compound [2]), α-cyperone (Compound [3]), isocyperol (Compound [4]), and caryophyllene α-oxide (Compound [5]), respectively.

Further, the compound represented by Chemical Formula 6 is designated as 3α-methoxyeudesma-4,11-diene (Compound [6]) or 7-methoxy-4a,8-dimethyl-2-(prop-1-en-2-yl)-1,2,3,4,4a,5,6,7-octahydronaphthalene (Compound [6]).

Six types of the compounds have an estrogenic activity, and therefore, a composition comprising the same can be used for the prevention or treatment of menopausal disorders which are caused by a decline of estrogen. In particular, the compounds represented by Chemical Formulae 1, 2, and 6 are characterized in that, when they are administered together with estrogen, they increase the estrogenic activity at a low level of estrogen, whereas they prevent an excessive increase of estrogenic activity at a high level of estrogen. Accordingly, there is an advantage that they can be used as a therapeutic agent for menopausal disorders capable of minimizing side-effects such as breast cancer caused by excessive estrogenic activity, etc.

The compounds of Chemical Formulae 1 to 6 may be commercially available or obtained by the known preparation methods thereof. Further, they can be separated and purified from plants containing the compounds. For example, they can be separated and purified from *Cyperus rotundus*, and specifically, they can be separated by suspending a C1-C4 alcohol extract of *Cyperus rotundus* in distilled water, fractionating it with hexane, and then applying the hexane fraction to silica gel chromatography, but is not limited thereto.

The compounds of Chemical Formulae 1 to 6 exhibit estrogenic activity, and therefore, the compounds or pharmaceutically acceptable salts thereof can be used for the prevention or treatment of menopausal disorders.

As used herein, the term "pharmaceutically acceptable salts" refers to a salt, composed of a cation and an anion with electrical attraction therebetween. In a form used pharmaceutically. Typically, metal salts, and salts with organic bases, inorganic acids, organic acids, and basic or acidic amino acids may be used. For example, metal salts such as alkali metal salts (sodium salt, potassium salt, etc.), alkaline earth metal salts (calcium salt, magnesium salt, barium salt, etc.), and aluminum salt; salts with organic bases, such as triethylamine, pyridine, picoline, 2,6-lutidine, ethanolamine, diethanolamine, triethanolamine, cyclohexylamine, dicyclohexylamine, N,N-dibenzylethylene diamine, etc.; salts with inorganic acids, such as hydrochloric acid, hydrobromic acid, nitric acid, sulfuric acid, phosphoric acid, etc.; salts with organic acids, such as formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc.; salts with basic amino acids, such as arginine, lysine, ornitine, etc.; and salts with acidic amino acids, such as aspartic acid, glutamic acid, etc. may be used. The compounds of Chemical Formulae 1 to 6 according to the present invention can be converted to salts thereof by a typical method.

Further, the compounds according to the present invention may contain asymmetric centers, and therefore they may exist as (R) or (S) isomers, racemates, diastereomeric mixtures, and individual diastereomers. All of the isomers and mixtures are included in the scope of the present invention.

In the present invention, it was confirmed that the extract of *Cyperus rotundus* or the fraction thereof exhibits estrogenic efficacy, and this estrogenic efficacy is attributed to the compounds represented by Chemical Formulae 1 to 6. Since the compounds represented by Chemical Formulae 1 to 6 are compounds which are included in *Cyperus rotundus*, and exhibit excellent estrogenic activity, the extract of *Cyperus rotundus* which includes the compounds by extraction, or the fraction thereof can be used for the prevention or treatment of menopausal disorders.

As used herein, the term "*Cyperus rotundus*" is a perennial plant belonging to the family of the Cyperaceae, characterized by rhizomes growing laterally and tubers in the apex of the rhizome.

As used herein, the term "extract of *Cyperus rotundus*" refers to a substance which is obtained by extracting *Cyperus rotundus*. With respect to the objects of the present invention, the extract of *Cyperus rotundus* is preferably a substance which is obtained by extracting *Cyperus rotundus* so as to include the compounds represented by Chemical Formulae 1 to 6. The extract of *Cyperus rotundus* can be obtained by extraction using water, C1-C4 alcohols, or organic solvents. Specifically, the extract of *Cyperus rotundus* is a C1-C4 alcohol extract of *Cyperus rotundus*, but is not limited thereto. An example of the C1-C4 alcohol includes methanol, ethanol, butanol, etc.

As used herein, the term "fraction of the extract of *Cyperus rotundus*" refers to a fraction extract which is obtained by extracting the extract of *Cyperus rotundus* using an organic solvent or a fraction extract which is obtained by purifying the extract by chromatography. With respect to the objects of the present invention, the fraction of the extract of *Cyperus rotundus* is a fraction of *Cyperus rotundus* extract, which is prepared so as to include one or more of the compounds represented by Chemical Formulae 1 to 6, and preferably an organic solvent fraction of the C1-C4 alcohol extract of *Cyperus rotundus*. The organic solvent may be isopropanol, butanol, ethylene, acetone, hexane, ether, chloroform, ethyl acetate, butyl acetate, dichloromethane, N,N-dimethyl formamide (DMF), dimethyl sulfoxide (DMSO), 1,3-buthylene glycol, propylene glycol, or a solvent mixture thereof, but is not limited thereto.

A hexane fraction of the C1-C4 alcohol extract of *Cyperus rotundus* comprises all of the compounds of Chemical Formulae 1 to 6 which exhibit estrogenic efficacy, and therefore, the hexane fraction may exhibit excellent estrogenic efficacy.

In one embodiment of the present invention, a hexane fraction of *Cyperus rotundus* methanol extract was prepared as the fraction of the *Cyperus rotundus* extract comprising the compound represented by any one of Chemical Formulae 1 to 6 (Example 1). The fraction includes all of the compounds of Chemical Formulae 1 to 6 which exhibit estrogenic activity, and therefore, it can be used in the prevention or treatment of menopausal disorders (FIGS. 2 and 4 to 7).

As used herein, the term "menopausal disorders" refers to a disease caused by a drop of the female hormone estrogen. Menopausal disorders also includes diseases that occur in estrogen-deficient patients due to other causes such as oophorectomy or a decline in ovarian function, as well as in climacteric women due to menopause. Estrogen is a hormone having various functions of helping blood circulation, body weight regulation, bone maintenance as well as female sexual characteristics. Estrogen deficiency causes many symptoms, for example, it may be accompanied by one or more symptoms selected from the group consisting of hot flashes, sudation, skin dryness, vaginal dryness, vaginal atrophy, atrophy of the lower urinary tract, dyspareunia, vaginitis, cystitis, dysuria, urinary urgency, attention deficit disorder, short-term memory impairment, anxiety, nervousness, memory loss, hypoactive sexual desire disorder, myalgia, arthralgia, and osteoporosis, but is not limited thereto.

As used herein, the term "prevention" refers to any action resulting in the suppression or delay of the onset of menopausal disorders owing to the administration of the composition according to the present invention.

As used herein, the term "treatment" refers to any action resulting in improvements in symptoms of menopausal disorders or the beneficial alteration of menopausal disorders owing to the administration of the composition according to the present invention.

As used herein, the term "subject" means all animals including monkeys, cattle, horses, sheep, pigs, chickens, turkeys, quails, cats, dogs, mice, rats, rabbits, or guinea pigs as well as humans who have already had menopausal disorders or have a possibility of having menopausal disorders. The above disease can be effectively prevented or treated by administering the composition of the present invention, the *Cyperus rotundus* extract comprising the same, or the fraction thereof to the subject.

As used herein, the term "administration" means introduction of a predetermined substance into a patient by a certain suitable method. The administration route in the present invention may be any of the common routes, as long as it is able to reach a desired tissue. The administration route may be intraperitoneal, intravenous, intramuscular, subcutaneous, intracutaneous, oral, topical, intranasal, intrapulmonary, or rectal route, but is not limited thereto. In addition, it may be administered using a certain apparatus capable of transporting the active ingredient of the present invention into a target cell.

The compound according to the present invention, the extract of *Cyperus rotundus* comprising the same, or the fraction thereof can be used as a pharmaceutical composition together with a pharmaceutically acceptable carrier, excipient, or diluent.

The pharmaceutical composition may have any one formulation selected from the group consisting of a tablet, a pill, a powder, a granule, a capsule, a suspension, a liquid for internal use, an emulsion, a syrup, a sterilized aqueous solution, a non-aqueous solvent, a suspension, an emulsion, a lyophilized formulation, and a suppository, and may be prepared in a variety of oral or parenteral formulations. For preparation into formulations, a diluent or an excipient, such as a typical filler, a bulking agent, a binder, a wetting agent, a disintegrating agent, or a surfactant, may be used. Examples of a solid formulation for oral administration include a tablet, a pill, powder, a granule, and a capsule, and these solid formulations are prepared by mixing one or more compounds with at least one excipient, for example, starch, calcium carbonate, sucrose, lactose, gelatin, etc. In addition to the simple excipient, a lubricant, such as magnesium stearate, talc, etc. is used. As a liquid formulation for oral administration, a suspension, a liquid for internal use, an emulsion, a syrup or the like may be used, and in addition to frequently used water and liquid paraffin, various other excipients, for example, a wetting agent, a sweetener, a flavoring agent, a preserving agent or the like may be included. As a formulation for parenteral administration, a sterilized aqueous solution, a non-aqueous solvent, a suspension, an emulsion, a lyophilized formulation, or a suppository formulation may be included. As the non-aqueous solvent or the suspension, propylene glycol, polyethylene glycol, a plant oil such as olive oil, an injectable ester such as ethylolate or the like may be used. As a base for suppositories, witepsol, macrogol, tween 61, cacao butter, laurin butter, glycerogelatin or the like may be used.

The compound according to the present invention, the extract of *Cyperus rotundus* comprising the same, or the fraction thereof may be administered in a therapeutically effective amount.

As used herein, the phrase "therapeutically effective amount" refers to an amount sufficient to treat the disease at a reasonable benefit/risk ratio applicable to any medical treatment. An effective dose level may vary depending on a variety of factors including the type, severity, age, and sex of the subject, the type of disease, drug activity, drug sensitivity, administration time, administration route, discharge ratio, treatment period, and co-administered drugs, and other factors well known in the medical field. The composition of the present invention may be administered alone or in combination with other therapeutics, and its co-administration with the conventional therapeutics may be carried out simultaneously or sequentially. Single or multiple dosages are possible. It is important to use the composition in the minimum possible amount sufficient to obtain the greatest effect without side effects, considering all the factors, and the amount can be easily determined by those skilled in the art. The preferred administration dose of (a) or (b) of the present invention may differ depending on a patient's condition and body weight, severity of the disease, type of the drug, administration route, and period. The administration may be performed once or several times per day. The composition may be administered into mammals such as rats, livestock, humans, etc. via various routes. All types of administration mode typically used in the art may be contemplated without limitation. For example, oral, rectal, or intravenous, intramuscular, subcutaneous, intracervical or intracerebroventricular routes may be taken.

In one embodiment of the present invention, a hexane fraction of the methanol extract of *Cyperus rotundus* was demonstrated as a fraction of the extract of *Cyperus rotundus* having a high estrogenic activity (Example 1 and FIG. 2), and 7 types of compounds showing the estrogenic activity was investigated from the hexane fraction (Example 2, FIG. 1). Among the compounds, in particular, the compounds represented by Chemical Formulae 1, 2, and 6 (Compounds [1], [2] and [6]) show an estrogen receptor-mediated estrogenic activity (FIGS. 5A and 5B). It was found that when high concentrations of estrogen were treated, the compounds lowered the estrogenic activity (FIGS. 6A and 6B), and when low concentrations of estrogen were treated, the compounds increased the estrogenic activity (FIG. 7), suggesting that the compounds can be used for controlling estrogenic activity, and therefore used in the development of estrogen agents with fewer side-effects. Accordingly, the compound or a pharmaceutically acceptable salt thereof can be used for the prevention and treatment of menopausal disorders.

Another aspect of the present invention provides a compound represented by the following Chemical Formula 6 or a pharmaceutically acceptable salt thereof.

[Chemical Formula 6]

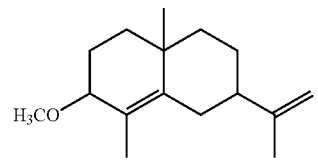

A pharmaceutically acceptable salt is the same as described above.

In the present invention, a novel sesquiterpenoid compound represented by Chemical Formula 6 capable of exhibiting both the estrogenic activity and anti-allergic activity was investigated from particular fractions of the extract of *Cyperus rotundus* which exhibits the estrogenic activity and anti-allergic activity (FIG. 1). The compound represented by Chemical Formula 6 is designated as 3α-methoxyeudesma-4,11-diene (Compound [6]) or 7-methoxy-4a,8-dimethyl-2-(prop-1-en-2-yl)-1,2,3,4,4a,5,6,7-octahydronaphthalene (Compound [6]). The compound represented by Chemical Formula 6 exhibits the estrogenic activity and anti-allergic activity (Table 1), and therefore, it can be used for the prevention or treatment of menopausal disorders caused by a decline of estrogen and allergic disease. In particular, the compound has characteristics that it increases the estrogenic activity at a low level of estrogen whereas it prevents excessive increase of estrogenic activity at a high level of estrogen, indicating that the compound is a compound capable of minimizing side-effects such as breast cancer caused by excessive estrogenic activity, etc. (FIGS. 6B and 7B). Accordingly, the compound or a pharmaceutically acceptable salt thereof can be used for the prevention and treatment of menopausal disorders or allergic disease.

Still another aspect of the present invention provides a pharmaceutical composition for the prevention or treatment of a menopausal disorder, comprising (a) the compound represented by Chemical Formula 6 or a pharmaceutically acceptable salt thereof, or (b) an extract of *Cyperus rotundus* comprising (a) or the fraction thereof as an active ingredient.

The compound represented by Chemical Formula 6, a pharmaceutically acceptable salt thereof, the extract of *Cyperus rotundus*, the fraction of the extract of *Cyperus rotundus*, menopausal disorder, prevention and treatment are as described above.

Still another aspect of the present invention provides an estrogen agent comprising the compound represented by Chemical Formula 6 or a pharmaceutically acceptable salt thereof as an active ingredient.

The compound represented by Chemical Formula 6 or a pharmaceutically acceptable salt thereof are the same as described above.

The compound represented by Chemical Formula 6 exhibits the estrogenic activity, and therefore, a composition comprising the same can be used as an estrogen agent or supplement.

Still another aspect of the present invention provides a food composition for the prevention or improvement of menopausal disorders, comprising (a) the compound represented by Chemical Formula 6 or a pharmaceutically acceptable salt thereof, or (b) an extract of *Cyperus rotundus* comprising (a) or the fraction thereof as an active ingredient.

The compound represented by Chemical Formula 6, a pharmaceutically acceptable salt thereof, the extract an extract of *Cyperus rotundus*, the fraction of the extract an extract of *Cyperus rotundus*, menopausal disorder, and prevention are the same as described above.

As used herein, the term "improvement" refers to any action resulting in improvements in symptoms of menopausal disorders or the beneficial alteration of menopausal disorders owing to the administration of (a) or (b).

Further, the food composition for the prevention or improvement of menopausal disorders can be also called as an estrogen-enhanced food composition.

The compound represent by Chemical Formula 6 has the estrogenic activity, and therefore, the compound or a pharmaceutically acceptable salt thereof can be added to the food composition for the purpose of preventing or improving menopausal disorders. When the compound or a pharmaceutically acceptable salt thereof is used as a food additive, it can be added at it is or together with other foods or components. Further, the addition amount thereof can be properly determined according to the purpose of use.

The type of the food of the present invention is not particularly limited. Examples of the food, to which the compound or a pharmaceutically acceptable salt thereof can be added, include meat, sausage, bread, chocolate, candy, snack, cookie, pizza, instant noodle, other noodles, chewing gum, dairy products including ice-cream, various kinds of soup, beverage, tea, drink, alcoholic beverages, and vitamin complex, etc., and includes all kinds of typical foods, and also foods used as a feed for animals.

In addition to the above ingredients, the food composition of the present invention may include various nutrients, vitamins, electrolytes, a flavor, a coloring agent, pectic acid and a salt thereof, alginic acid and a salt thereof, an organic acid, a protective colloid thickener, a pH adjuster, a stabilizer, a preservative, glycerin, alcohol, a carbonating agent used for a carbonated drink, etc. Also, the composition of the present invention may include flesh for the preparation of natural fruit juice, fruit juice drinks, and vegetable drinks. The food may be also prepared in the formulation of a tablet, granule, powder, capsule, liquid solution, pill, etc. according to a known preparation method. Except for including the compound represented by Chemical Formula 6 of the present invention or a pharmaceutically acceptable salt thereof, there is no particular limitation in other ingredients, and typical additional ingredients such as various flavoring agent, natural carbohydrates, etc. may be included.

Still another aspect of the present invention provides a quasi-drug composition for the prevention or improvement of menopausal disorders, comprising (a) the compound represented by Chemical Formula 6 or a pharmaceutically acceptable salt thereof, or (b) an extract of *Cyperus rotundus* comprising (a) or the fraction thereof as an active ingredient.

The compound represented by Chemical Formula 6, a pharmaceutically acceptable salt thereof, the extract of *Cyperus rotundus*, the fraction of the extract of *Cyperus rotundus*, menopausal disorder, prevention and improvement are as described above.

Specifically, the ingredient a) or b) can be added to the quasi-drug composition for the purpose of preventing or improving menopausal disorders, and in this regard, it can be used together with other quasi-drug ingredients, and properly used according to a typical method. The mixing amount of the ingredient a) or b) can be properly determined according to the purpose of use (prevention, health or therapeutic treatment).

Preferably, the quasi-drug composition may be a disinfectant cleaner, a shower-foam, a mouthwash, a wet tissue, a detergent soap, a hand-wash, a humidifier filler, a mask, an ointment or a filter filler, but is not limited thereto.

Still another aspect of the present invention provides a pharmaceutical composition for the prevention or treatment of an allergic disease, comprising (a) the compound represented by Chemical Formula 6 or a pharmaceutically acceptable salt thereof, or (b) an extract of *Cyperus rotundus* comprising (a) or the fraction thereof as an active ingredient.

The compound represented by Chemical Formula 6, a pharmaceutically acceptable salt thereof, the extract of *Cyperus rotundus*, and the fraction of the extract of *Cyperus rotundus* are the same as described above.

With respect to the objects of the present invention, the extract of *Cyperus rotundus* or the fraction thereof may exhibit excellent anti-allergic efficacy, because it includes the compound of Chemical Formula 6 showing the anti-allergic efficacy.

As used herein, the term "prevention" refers to any action resulting in the suppression or delay of the onset of allergic diseases owing to the administration of the composition according to the present invention.

As used herein, the term "treatment" refers to any action resulting in improvements in symptoms of allergic diseases or the beneficial alteration of allergic diseases owing to the administration of the composition according to the present invention.

As used herein, the term "allergic disease" refers to a disease having symptoms which are generated by released substances resulting from a biochemical phenomenon showing a specific and altered reaction against a foreign substance (antigen, allergen). Allergy is a pathological process in the body, resulting from the etiology antigen-antibody reaction, and allergy is generally classified into 1 to 4 types according to time taken for the reaction and complement mediation. The composition can be used for the prevention or treatment of allergic diseases known in the art, and for example, it can be used for the prevention or treatment of atopy, asthma, hypersensitivity, allergic rhinitis, allergic conjunctivitis, allergic dermatitis, contact dermatitis, hives, insect allergies, food allergies or drug allergies, but is not limited thereto.

In one embodiment of the present invention, to examine anti-allergic efficacy of the compound (Compound [6]) represented by Chemical Formula 6, β-hexosaminidase release assay was performed. As a result, Compound [6] showed an inhibitory effect on degranulation, and thus Compound [6] was found to have the anti-allergic efficacy (Table 1).

Still another aspect of the present invention provides a method for preventing or treating an allergic disease in a subject in need thereof, comprising administering (a) the compound represented by Chemical Formula 6 or a pharmaceutically acceptable salt thereof, or (b) an extract of *Cyperus rotundus* comprising (a) or the fraction thereof to the subject.

The compound represented by Chemical Formula 6, a pharmaceutically acceptable salt thereof, the extract of *Cyperus rotundus*, the fraction of the extract of *Cyperus rotundus*, subject, administration, allergic disease, prevention and treatment are as described above.

Still another aspect of the present invention provides a food composition for the prevention or improvement of allergic disease, comprising (a) the compound represented by Chemical Formula 6 or a pharmaceutically acceptable salt thereof, or (b) an extract of *Cyperus rotundus* comprising (a) or the fraction thereof as an active ingredient.

The compound represented by Chemical Formula 6, a pharmaceutically acceptable salt thereof, the extract of *Cyperus rotundus*, the fraction of the extract of *Cyperus rotundus*, subject, administration, allergic disease, prevention and food are the same as described above.

As used herein, the term "improvement" refers to any action resulting in improvements in symptoms of allergic diseases or the beneficial alteration of allergic diseases owing to the administration of (a) or (b).

Still another aspect of the present invention provides a quasi-drug composition for the prevention or improvement of allergic disease, comprising (a) the compound represented by Chemical Formula 6 or a pharmaceutically acceptable salt thereof, or (b) an extract of *Cyperus rotundus* comprising (a) or the fraction thereof as an active ingredient.

The compound represented by Chemical Formula 6, a pharmaceutically acceptable salt thereof, the extract of *Cyperus rotundus*, the fraction of the extract of *Cyperus rotundus*, subject, administration, allergic disease, prevention and improvement are the same as described above.

Still another aspect of the present invention provides a method for preventing or treating menopausal disorders or allergic diseases, comprising administering (a) an organic solvent fraction of the C1-C4 alcohol extract of *Cyperus rotundus*, or (b) a fraction which is obtained by applying the alcohol extract to hydrophobic chromatography and then eluting it with C1-C4 alcohol, to a subject in need thereof.

The *Cyperus rotundus*, the extract of *Cyperus rotundus*, the fraction of the extract of *Cyperus rotundus*, subject, administration, menopausal disorders, allergic disease, prevention and treatment are the same as described above.

In the present invention, it was confirmed that the organic solvent fraction of the C1-C4 alcohol extract of *Cyperus rotundus*, or the fraction eluted from the extract by hydrophobic chromatography has a remarkably high estrogenic activity or anti-allergic activity, compared to other fractions (Experimental Examples 1 and 3), and therefore, the fraction can be used for the prevention or treatment of menopausal disorders or allergic diseases.

Specifically, the organic solvent fraction of the C1-C4 alcohol extract of *Cyperus rotundus* can be obtained by extracting *Cyperus rotundus* with C1-C4 alcohol, preferably, methanol to obtain an alcohol extract, and then by suspending the alcohol extract in distilled water, followed by fractionation with a dichloromethane or butanol solution according to the typical method (Example 1), but is not limited thereto.

Specifically, the fraction eluted from the C1-C4 alcohol extract of *Cyperus rotundus* by hydrophobic chromatography can be obtained by extracting *Cyperus rotundus* with C1-C4 alcohol, preferably, methanol to obtain an alcohol extract, and then by subjecting the alcohol extract to hydrophobic chromatography such as Diaion HP-20 column chromatography, followed by elution with C1-C4 ethanol, preferably, a 70 to 95% ethanol solution (Example 1), but is not limited thereto.

In one embodiment of the present invention, the fraction eluted from the ethanol extract of *Cyperus rotundus* by hydrophobic chromatography was found to show high estrogenic efficacy (Experimental Example 1)

Hereinafter, the present invention will be described in detail with reference to the following Examples. However, these Examples are for illustrative purposes only, and the invention is not intended to be limited by these Examples.

Example 1: Preparation of Extracts of *Cyperus rotundus* and Fractions Thereof (1) Preparation of a Methanol Extract of *Cyperus rotundus* and Organic Solvent Fractions Thereof

*Cyperus rotundus* was cut finely, and then immersed in cold methanol (MeOH) at room temperature twice, and immersed in a warm aqueous solution at 50° C. once, and then concentrated to obtain a methanol extract. In detail, 3.0 kg of *Cyperus rotundus* was immersed in 4 L of methanol at room temperature twice, and extracted at 50° C. once, filtered, and then concentrated under reduced pressure to obtain 283.56 g of a methanol extract (MeOH-extract).

The methanol extract was suspended in 2.4 L of distilled water and fractionated with hexane (34.61 g), dichloromethane ($CH_2Cl_2$) (10.71 g), ethyl acetate (EtOAc) (3.70 g), n-butanol (BuOH) (18.31 g), and distilled water ($H_2O$) (204.51 g) in this order according to the typical method so as to obtain 5 fractions.

(2) Preparation of an Ethanol Extract of *Cyperus rotundus* and Column Fractions Thereof 1.2 kg of *Cyperus rotundus* was extracted with 1.6 L of ethanol at room temperature three times, and filtered, and then concentrated under reduced pressure to obtain 57.96 g of an ethanol extract. The ethanol extract thus obtained was subjected to a Diaion HP-20 column, and eluted with distilled water ($H_2O$), a mixture of distilled water-ethanol and acetone in this order to obtain each fraction of distilled water (38.9 g), 30% ethanol (3.5 g), 50% ethanol (1.9 g), 70% ethanol (3.7 g), 95% ethanol (6.55 g) and acetone (3.63 g).

Example 2: Separation of 7 Types of Active Ingredients from Extract of *Cyperus rotundus*

The hexane fraction of Example 1 was subjected to a silica gel column, and then eluted using hexane/dichloromethane=3:1, 1:1, dichloromethane, hexane/dichloromethane/methanol=10:10:1 as elution solvents to obtain 14 fractions.

Compound [7] was separated and purified from repeated silica gel column (hexane/dichloromethane=3:1, 5:1) and RP-18 column chromatographies (88% MeCN) of the fraction 8.

The third fraction obtained from the faction 8 was subjected to Lobar A silica gel column (hexane/dichloromethane=1:1, 1:2) and recycling HPLC using JAIGEL-1H and 2H column ($CHCl_3$) to separate Compound [1].

The fraction 9 was subjected to silica gel column chromatography using a solvent mixture of hexane/ethyl acetate (50:1~1:1) to obtain 22 fractions, and among them, the eighth fraction was subjected to RP-18 column chromatography using 80% MeCN to separate Compound [5]. The tenth fraction was subjected to RP-18 column (80% MeCN) to separate Compound [3], and the fourteenth fraction was subjected to RP-18 (85% MeCN) and silica gel column chromatography (hexane/ethyl acetate=20:1, 10:1) to separate Compound [4]. The seventh fraction of the fraction 9 was subjected to Lobar A silica gel column (hexane/ethyl acetate=7:1, 1:1) and recycling HPLC using JAIGEL-1H and 2H column ($CHCl_3$) to separate Compound [2].

7 types of the substances separated and purified from active fractions of the extract of *Cyperus rotundus* were subjected to instrumental analysis including 1D, 2D-NMR so as to determine their structures.

In detail, Compound [1] was determined as 4α,5α-oxidoeudesm-11-en-3-one, Compound [2] as cyper-11-ene-3,4-dione, Compound [3] as α-cyperone, Compound [4] as isocyperol, Compound [5] as caryophyllene α-oxide, and Compound [6] as cyperotundone. Their structures were determined by comparison of those in the literature records and the data of instrumental analysis. Structures of Compounds [1] to [6] are shown in FIG. 1. Further, Compounds [1] and [2] were demonstrated as compounds that were first separated from natural sources. The instrumental analysis data of demonstrated Compounds [1] to [6] and the literature records compared therewith are as follows.

[1] 4α,5α-oxidoeudesm-11-en-3-one: Colorless oil; $^1$H-NMR ($CDCl_3$, 500 MHz) δ 1.05 (3H, s, H-15), 1.40 (3H, s, H-14), 1.75 (3H, br s, H-13), 4.74 (1H, d, J=1.0 Hz, H-12a), 4.75 (1H, d, J=1.5 Hz, H-12b); $^{13}$C-NMR ($CDCl_3$, 125 MHz) δ 11.3 (C-15), 20.7 (C-14), 20.8 (C-13), 26.4 (C-8), 26.1 (C-8), 31.4 (C-6), 31.8 (C-1), 33.3 (C-9), 33.9 (C-10), 38.0 (C-2), 43.0 (C-7), 65.5 (C-4), 72.0 (C-5), 109.3 (C-12), 149.0 (C-11), 207.9 (C-3); EI-GC/MS m/z 234 [M]+, 206, 191, 163, 149, 137, 109, 67, 41.

*Phytochemistry*, 15, 1265~1266 (1976)

[2] cyper-11-ene-3,4-dione: Colorless oil; $^1$H-NMR ($CDCl_3$, 500 MHz) δ 1.18 (3H, s, H-14), 1.75 (3H, br s, H-13), 2.12 (3H, s, H-15), 4.73 (1H, br s, H-12a), 4.75 (1H, d, J=1.5 Hz, H-12b); $^{13}$C-NMR ($CDCl_3$, 125 MHz) δ 21.3 (C-14), 22.0 (C-15), 26.6 (C-8), 29.9 (C-13), 30.7 (C-2), 33.2 (C-9), 36.0 (C-6), 38.2 (C-1), 41.3 (C-7), 42.5 (C-10), 71.2 (C-5), 109.2 (C-11), 149.3 (C-12), 209.0 (C-4), 217.6 (C-3); EI-GC/MS m/z 234 [M]+, 206, 191, 177, 164, 159, 149, 145, 139, 131, 123, 110, 91, 79, 67.

*Chem. Pharm. Bull.* 15(9), 1395~1404 (1967).

[3] α-cyperone: Colorless oil; $^1$H-NMR ($CDCl_3$, 500 MHz) δ 1.24 (3H, s, H-14), 1.79 (6H, m, H-12, 15), 4.80 (2H, brs, H-13); $^{13}$C-NMR ($CDCl_3$, 125 MHz) δ 11.1 (C-15), 20.9 (C-13), 22.8 (C-8), 27.1 (C-6), 33.2 (C-2), 34.0 (C-1), 36.1 (C-10), 37.7 (C-14), 42.2 (C-9), 46.2 (C-7), 109.4 (C-12), 129.1 (C-4), 149.4 (C-5), 162.4 (C-11), 199.3 (C-3); EI-GC/MS m/z 218 [M]+ (100), 203 (49) 190 (16) 175 (58) 161 (69) 147 (74), 133 (53), 121 (53), 119 (57), 105 (58), 91 (80), 79 (60), 67 (40).

*Tetrahedron*, 48, 3121-3130 (1992).

[4] isocyperol: Colorless oil; $^1$H-NMR (CDCl3, 500 MHz) δ 0.72 (3H, s, H-15), 1.76 (3H, br s, H-12), 4.30 (1H, br s, H-3), 4.60 (1H, t, J=2.0 Hz, H-14a), 4.71 (1H, br s, H-12a), 4.73 (1H, br s, H-12b), 4.94 (1H, br t, J=1.5 Hz, H-14b); $^{13}$C-NMR ($CDCl_3$, 125 MHz) δ 15.8 (C-15), 21.3 (C-13), 27.0 (C-8), 29.3 (C-6), 30.0 (C-2), 36.0 (C-1), 36.1 (C-10), 41.0 (C-9), 43.9 (C-7), 46.0 (C-5), 73.8 (C-3), 108.5 (C-12), 109.2 (C-14), 150.9 (C-11), 152.2 (C-4); EI-GC/MS m/z 220 [M]+ (18), 205 (15), 202 (13), 187 (29), 159 (31), 148 (48), 133 (47), 119 (48), 107 (100), 91 (89), 79 (86), 67 (72).

*Chem. Pharm. Bull.*, 31, 3391-3396 (1983).

[5] caryophyllene α-oxide: Colorless needles; $^1$H-NMR ($CDCl_3$, 500 MHz) δ 0.99 (3H, s, H-12), 1.02 (3H, s, H-13), 1.21 (3H, s, H-14), 4.87 (1H, m, H-15α), 4.99 (1H, m, H-15β); $^{13}$C-NMR ($CDCl_3$, 125 MHz) δ 21.7 (C-13), 27.2 (C-2), 29.8 (C-7), 30.0 (C-12), 30.3 (C-6), 34.0 (C-11), 39.2 (C-3), 39.8 (C-10), 48.8 (C-9), 50.7 (C-1), 59.3 (C-4), 63.7 (C-5), 112.8 (C-15), 151.8 (C-8); EI-GC/MS m/z 220 [M]+ (2), 205 (7), 187 (8), 177 (14), 161 (17), 149 (20), 135 (21), 121 (40), 109 (54), 93 (87), 79 (100), 69 (61), 55 (42), 41 (69).

*Phytochem.*, 40, 125-128 (1995).

[6] 3α-methoxyeudesma-4,11-diene: Colorless oil; $^1$H-NMR ($CDCl_3$, 500 MHz) δ 1.04 (3H, s, H-15), 1.74 (3H, brs, H-14), 1.76 (3H, brs, H-13), 2.56 (1H, m, H-6a), 3.37 (1H, m, H-3), 3.40 (3H, s, OMe), 4.72 (2H, brs, H-12); $^{13}$C-NMR (CDCl$_3$, 125 MHz) δ 17.5 (C-14), 21.1 (C-13), 22.3 (C-9), 23.2 (C-15), 27.6 (C-2), 31.1 (C-6), 34.7 (C-1), 35.0 (C-8), 42.3 (C-10), 46.5 (C-7), 57.3 (OMe), 79.3 (C-3), 108.5 (C-12), 124.8 (C-4), 140.6 (C-5), 150.7 (C-11); EI-GC/MS m/z 234 [M]+ (56), 219 (77), 202 (17), 187 (29), 152 (100), 138 (90), 119 (31), 105 (50), 91 (49), 79 (31).

[7] cyperotundone: Colorless needles; $^1$H-NMR (CDCl$_3$, 500 MHz) δ 0.64 (3H, d, J=6.5 Hz, H-15), 0.75 (3H, s, H-13), 1.11 (3H, s, H-12), 1.73 (3H, t, J=1.2 Hz, H-14), 2.02 (1H, d, J=17.5 Hz, H-2a), 2.16 (1H, d, J=17.5 Hz, H-2b), 2.18 (1H, m, H-10), 2.32 (1H, d, J=18.0 Hz, H-6a), 2.61 (1H, dd, J=18.0, 7.0 Hz, H-6b); $^{13}$C-NMR (CDCl$_3$, 125 MHz) δ 8.3 (C-14), 16.8 (C-15), 19.5 (C-12), 24.9 (C-13), 27.0 (C-8), 28.5 (C-9), 30.5 (C-6), 33.8 (C-10), 41.1 (C-2), 41.7 (C-11), 45.5 (C-7), 58.8 (C-1), 133.4 (C-4), 181.7 (C-5), 210.9 (C-3); EI-GC/MS m/z 218 [M]+ (100), 203 (16), 189 (12), 175 (44), 161 (30), 147 (43), 133 (34), 119 (28), 105 (30), 91 (33), 77 (18).

*Magn. Reson. Chem.*, 47, 527-531 (2009).

Experimental Example 1: E-Screen Assay for Estrogenic Activities of Extracts of *Cyperus rotundus* and Fractions Thereof (1) E-Screen Assay To confirm estrogenic activities of the extracts of *Cyperus rotundus* and the fractions thereof, E-screen assay was performed.

E-screen assay is a method of measuring estrogenic action of a substance, i.e., a method of utilizing the growth effect of MCF-7-bus, a breast cancer cell line with endogenous estrogen receptors (ER) expressed therein, which is stimulated by an estrogenic substance. In the present invention, estrogenic activities of the methanol extract and the organic solvent fraction thereof, the ethanol extract and the column fraction thereof were examined by E-screen assay.

In detail, MCF-7-bus cells were cultured in a 5% FBS DMEM medium and seeded in a 48-well plate at a density of 5×10$^3$ cells/well. The cells were cultured in a CO$_2$ incubator at 37° C. for 48 hours, and then washed with a phenol red-free medium twice. The test materials were diluted with 5% CD-FBS DMEM at different concentrations, and then cells were treated therewith. The concentration of the solvent was in principle adjusted to 0.1%. After culturing for 144 hours (6 days), cells were fixed to the plate with TCA (Trichloroacetic acid) solution. The cells thus fixed were stained with SRB (Sulforhodamin B) dye, and the SRB dye remaining in the plate was removed by washing with acetic acid. The bound SRB dye was eluted from the cells with tris-base solution, and absorbance at 490 nm was measured to calculate the amount of SRB dye. Finally, estrogenic actions of the test materials were confirmed.

(2) Test of Estrogenic Activities of Extracts of *Cyperus rotundus* and Fractions Thereof First, among 5 fractions fractionated by solvent extraction, the hexane fraction, the dichloromethane fraction and the methanol extract, except the n-butanol fraction, the water fraction, and the ethyl acetate fraction having low reactivity, were used to examine their estrogenic activities, and the results are shown in FIG. 2.

As shown in FIG. 2, the methanol extract, the hexane fraction and the dichloromethane fraction showed effective estrogenic activity, and higher reactivities were observed in the order of methanol extract, hexane fraction, and dichloromethane (CH$_2$Cl$_2$) fraction.

Further, estrogenic actions of 6 fractions which were obtained by fractionating the ethanol extract of *Cyperus rotundus* using Diaion HP-20 column were examined, and the results are shown in FIGS. 3A and 3B.

As shown in FIGS. 3A and 3B, it was found that the acetone fraction, water fraction, 30% ethanol fraction, and 50% ethanol fraction showed low estrogenic actions, whereas 95% and 70% ethanol fractions, and ethanol extract showed high estrogenic actions.

Experimental Example 2: Test of Estrogenic/Anti-Estrogenic Actions of 6 Types of Sesquiterpenoid Compounds and Mechanisms Thereof (1) Test of Estrogenic Activities of Compounds [1] to [6]

Estrogenic activities of 7 types of compounds (Compounds [1] to [7]) which were separated from the hexane fractions and found to have excellent estrogenic activity in Experimental Example 1 were examined by E-screen assay in the same manner as in Experimental Example 1, and the results are shown in FIG. 4.

As shown in FIGS. 4A and 4B, all Compounds [1] to [7] of the present invention showed estrogenic activities, and in particular, Compound [1] showed excellent estrogenic activity.

(2) Test of Estrogenic Action Mechanisms of Compounds [1] and [2]

Action mechanisms of Compounds [1], [2], and [6] showing estrogenic activity were examined using tamoxifen.

In detail, Tamoxifen is a representative estrogen receptor antagonist, and in this experiment, in order to examine whether the test materials show the estrogen receptor-mediated estrogenic actions, the test materials were mixed with tamoxifen (10$^{-6}$M) and MCF-7 bus cells were treated with the mixture to perform e-screen assay, and the results are shown in FIG. 5.

As shown in FIGS. 5A and 5B, Compounds [1], [2], and [6] which showed high estrogenic activity as confirmed in (1) showed remarkably reduced activities by co-treatment with tamoxifen. That is, the activities of Compounds [1], [2], and [6] of the present invention were mediated by estrogen receptors, suggesting a possibility of estrogen supplements.

(3) Test of Selective Estrogen Receptor Modulator (SERM) Functions of Compounds [1], [2], and [6]

In addition to (1) and (2), the SERM functions of Compounds [1], [2], and [6] were examined by co-treatment with low or high concentration of estrogen.

In detail, to examine whether the test materials function as an antagonist of estrogen at excessively high level of estrogen in the body, the test materials were mixed with high concentration of estradiol (10$^{-7}$M) and MCF-7 bus cells were treated with the mixture. To examine whether the test materials function as an agonist of estrogen at estrogen deficiency in the body, the test materials were mixed with a low concentration of estradiol (10$^{-13}$M) and MCF-7 bus cells were treated with the mixture. Then, e-screen assay was performed.

As a result, it can be seen that Compounds [1], [2], and [6] separated from *Cyperus rotundus* function as an estrogen inhibitor when the level of estrogen in the body is excessively high (FIGS. 6A and 6B), and also function as an estrogen supplement when estrogen is deficient in the body (FIGS. 7A and 7B), indicating that the compounds properly control the estrogen level in the body.

Experimental Example 3: Test of Anti-Allergic Activities of Fractions of Extract of *Cyperus Rotundus*

In order to examine anti-allergic activities of the solvent fractions of the extract of *Cyperus rotundus*, β-hexosaminidase release assay was performed.

β-Hexosaminidase release assay is an experiment for examining anti-allergic activity by activating the RBL-2H3 cell line with an activating factor, treating the activated cells with an antigen, and then measuring the amount of released β-hexosaminidase to examine inhibitory effect on degranulation, and this assay was performed as follows.

In detail, the RBL-2H3 cell line was cultured in minimum essential media (hereinafter, referred to as EMEM) containing Eagle's salt supplemented with 15% fetal bovine serum and L-glutamine at 37° C. in a 5% $CO_2$ incubator. Adherent cells were suspended by Trypsin-EDTA, and separated, recovered for use in the experiment. The RBL-2H3 cell line was activated with an activating factor (Dinitrophenol-conjugated human serum albumin, (DNP-HSA)-specific IgE), and then the activated cells were treated with 200 ng/mL of an antigen (DNP-HSA), and 0, 6.25, 12.5, 25, 50, or 100 μg/mL of the fraction of the extract of *Cyperus rotundus* was treated, respectively. Cells were incubated for 30 minutes. As a positive control, 50 μg/mL of ketotifen was used. Thereafter, the amount of β-hexosaminidase released to the medium was measured using a microplate spectrophotometer. Inhibition of β-hexosaminidase release means prevention of degranulation of immune cells.

As shown in FIG. 8, strong anti-allergic activities were observed in a hexane fraction, a dichloromethane (MC, $CH_2Cl_2$) fraction, and an n-BuOH fraction among the solvent fractions of the methanol extract of *Cyperus rotundus*.

Experimental Example 4: Test of Anti-Allergic Activity of Compound [6]

Further, β-hexosaminidase release assay was performed to examine whether Compound [6] has the inhibitory effect on degranulation to show an anti-allergic activity, and the results are shown in the following Table 1.

TABLE 1

β-Hexosaminidase release assay for anti-allergic activity of Compound [6] (50 μg/ml)

| Compound | Degranulation-inhibitory activity (%, Mean ± SD) |
| --- | --- |
| Compound [6] | 41.7 ± 5.40 |
| Ketotifen | 50.5 ± 2.28 |

As shown in Table 1, Compound [6] of the present invention shows degranulation-inhibitory activity, and therefore, Compound [6] can be used for the prevention or treatment of allergic disease.

It will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims, and therefore all changes and modifications that fall within metes and bounds of the claims, or equivalents of such metes and bounds are therefore intended to be embraced by the claims.

EFFECT OF THE INVENTION

A sesquiterpenoid compound according to the present invention, the extracts of *Cyperus rotundus* comprising the same, or the fractions thereof exhibit excellent estrogenic activity or anti-allergic activity, and therefore, they can be used for the prevention or treatment of menopausal disorders caused by a decline in estrogen or allergic diseases.

What is claimed is:

1. A method for treating a menopausal disorder in a subject in need thereof, said method comprising administering an effective amount of a hexane fraction of a C1-C4 alcohol of *Cyperus rotundus* to the subject.

2. The method according to claim 1, wherein the menopausal disorder is accompanied by one or more symptoms selected from the group consisting of hot flashes, sudation, skin dryness, vaginal dryness, vaginal atrophy, atrophy of the lower urinary tract, dyspareunia, vaginitis, cystitis, dysuria, urinary urgency, attention deficit disorder, short-term memory impairment, anxiety, nervousness, memory loss, hypoactive sexual desire disorder, myalgia, arthralgia and osteoporosis.

* * * * *